US009115067B1

(12) United States Patent
Bunning et al.

(10) Patent No.: US 9,115,067 B1
(45) Date of Patent: Aug. 25, 2015

(54) PROCESS FOR THE MANUFACTURE OF ACROLEIN

(71) Applicant: Novus International Inc., St. Charles, MO (US)

(72) Inventors: Donald L. Bunning, South Charleston, WV (US); James D. Rolston, Friendswood, TX (US); David A. LaBrot, South Charleston, WV (US); Puvin Pichai, Friendswood, TX (US); John Patrick Dever, South Charleston, WV (US); Olan Stanley Fruchey, Hurricane, WV (US); Michael L. Hutchison, South Charleston, WV (US); Kevin Roy, South Charleston, WV (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 14/579,240

(22) Filed: Dec. 22, 2014

(51) Int. Cl.
*C07C 45/35* (2006.01)

(52) U.S. Cl.
CPC ..................... *C07C 45/35* (2013.01)

(58) Field of Classification Search
CPC ....................................... C07C 45/35
USPC ......................... 568/479, 476, 470
See application file for complete search history.

(56) References Cited

U.S. PATENT DOCUMENTS

| 4,031,135 | A | 6/1977 | Engelbach |
| 4,442,308 | A | 4/1984 | Arntz |
| 5,183,936 | A | 2/1993 | Etzkorn |
| 5,198,578 | A | 3/1993 | Etzkorn |
| 6,028,220 | A | 2/2000 | Wada |
| 6,057,481 | A | 5/2000 | Brockwell |
| 6,166,263 | A | 12/2000 | Etzkorn |
| 6,515,187 | B1 | 2/2003 | Schon |
| 6,545,178 | B1 | 4/2003 | Tanimoto |
| 7,019,176 | B2 | 3/2006 | Dieterle |
| 7,045,657 | B2 | 5/2006 | Yunoki |
| 7,115,776 | B2 | 10/2006 | Hammon |
| 7,119,227 | B2 | 10/2006 | Sakakura |
| 7,217,836 | B2 | 5/2007 | Watanabe |
| 7,265,250 | B2 | 9/2007 | Shin |
| 7,273,593 | B2 | 9/2007 | Olbert |
| 7,297,814 | B2 | 11/2007 | Yada |
| 7,361,791 | B2 | 4/2008 | Liang |
| 7,439,389 | B2 | 10/2008 | Dieterle |
| 7,518,015 | B2 | 4/2009 | Cremer |
| 7,541,490 | B2 | 6/2009 | Okazaki |
| 7,544,836 | B2 | 6/2009 | Jinno |
| 7,563,927 | B2 | 7/2009 | Ogawa |
| 8,178,718 | B2 | 5/2012 | Liang |
| 8,188,310 | B2 | 5/2012 | Cremer |
| 8,193,396 | B2 | 6/2012 | Lin |
| 8,242,308 | B2 | 8/2012 | Ho |
| 2011/0015432 | A1 | 1/2011 | Tanimoto |
| 2011/0172462 | A1 | 7/2011 | Ligon |
| 2011/0306788 | A1 | 12/2011 | Tanimoto |
| 2012/0095267 | A1 | 4/2012 | Macht |

FOREIGN PATENT DOCUMENTS

EP 0009545 B1 7/1979

*Primary Examiner* — Sikarl Witherspoon
(74) *Attorney, Agent, or Firm* — Polsinelli PC

(57) ABSTRACT

The invention generally relates to the manufacture of acrolein. In particular, the invention generally relates to a process for the continuous production of acrolein via the catalytic oxidation of propylene.

16 Claims, 2 Drawing Sheets

PROCESS FOR THE MANUFACTURE OF ACROLEIN

FIELD OF THE INVENTION

The invention generally relates to the manufacture of acrolein. In particular, the invention relates to a process for the continuous production of acrolein via the catalytic oxidation of propylene.

BACKGROUND OF THE INVENTION

Acrolein is an important starting material for several industrial chemical reactions. The process for producing acrolein involves two major steps: (1) catalytic oxidation of propylene to produce acrolein, and (2) recovery of the acrolein from the reaction products.

Acrolein is typically produced from the vapor-phase oxidation of propylene over a solid-phase catalyst. Conventionally in this reaction, propylene is mixed with air and steam and is passed over the catalyst one time under high temperature and modest pressure, namely a "single-pass" process. Operating conditions used in a single-pass process often achieve a high conversion of propylene, for example, often approaching over 95%. But the operating conditions used in reactors of single-pass processes achieve this high conversion at the expense of reaction selectivity. Moreover, running the reactor at the temperatures employed in single-pass processes typically decreases the life of the catalyst. Use of steam and air in the process also results in significant generation of wastewater and reaction gases that must be purged.

The recovery of acrolein having a high degree of purity from the reaction effluent gas stream is challenging and typically involves several pieces of expensive equipment. Overall, traditional recovery of acrolein involves scrubbing the reaction effluent gas stream with water or a water-solvent mixture in a first separation device to remove acrylic acid, polymeric compounds, and traces of acetic acid. The reaction effluent gas stream is then generally passed to an absorber, where an aqueous solution of acrolein is obtained by absorbing the gas into cold water. The off-gas must be purged as waste gas, because of the large volume of nitrogen contained in the air feed. The aqueous acrolein solution is then typically sent to a desorption column, where the solution is stripped to give crude acrolein. The bottom stream of this column is cooled and reused as an absorbent in the absorber column. The overhead stream from the desorber is distilled (i.e., fractionated) in a light ends column to remove some of the low-boiling byproducts, such as acetaldehyde. The acrolein stream is sent to a heavy ends column where the heavies are removed as the residue stream and the purified acrolein is taken as an overhead stream. This purified acrolein may be used in other industrial processes.

What is needed is a process for producing acrolein in a more efficient and cost effective manner with generation of fewer waste products. In particular, what is needed is a process having improved selectivity, improved overall yield, and improved catalyst life, while allowing isolation of pure acrolein having low levels of impurities without the need for all of the equipment used in traditional acrolein recovery.

SUMMARY OF THE INVENTION

Briefly, therefore, the present invention provides a process that is efficient and cost effective with generation of fewer waste products compared to traditional single pass acrolein processes. In this regard, the process of the present invention uses one recycle step to produce acrolein and a second recycle step to recover acrolein. Via use of the two recycle steps, the acrolein manufacturing process of the invention achieves improved selectivity, improved yield, improved catalyst life, reduced aqueous waste, reduced gaseous waste, and allows for recovery of higher purity acrolein with less capital expenditures compared to conventional processes.

As such, an iteration of the invention encompasses a continuous process for producing acrolein. The process generally comprises the following steps:

(a) feeding an initial gas stream comprising an oxygen source, and a propylene source to a reactor comprising a catalyst under conditions such that propylene is oxidized to produce a reaction effluent gas stream, the reaction effluent gas stream comprising acrolein, oxygen, propylene, carbon monoxide, carbon dioxide, acrylic acid, acetic acid, water, and acetaldehyde;

(b) feeding the reaction effluent gas stream to the bottom section of a first separation device, the condensable portion of the reaction effluent gas stream being condensed in the first separation device to provide an aqueous liquid stream and a recycle gas stream, the condensable portion of the reaction effluent gas stream becoming the aqueous liquid stream comprising acrolein, acrylic acid, acetic acid, water and acetaldehyde, the non-condensable portion of the reaction effluent gas stream becoming the recycle gas stream comprising oxygen, propylene, propane, carbon dioxide, and carbon monoxide;

(c) feeding a portion of the recycle gas stream to the reactor of step (a);

(d) feeding the aqueous liquid stream to a second separation device that fractionates the aqueous liquid stream into a low-boiling point impurity stream, an acrolein stream, and a liquid recycle stream, the low-boiling point impurity stream comprising acetaldehyde, the acrolein stream comprising substantially pure acrolein, and the liquid recycle stream comprising water, acetic acid, and acrylic acid; and (e) feeding a portion of the liquid recycle stream to the top of the first separation device of step (b), the liquid recycle stream comprising from about 20% to about 30% acrylic acid by weight.

Other features and iterations of the invention are detailed more fully below.

DETAILED DESCRIPTION OF THE INVENTION

Figure 1:
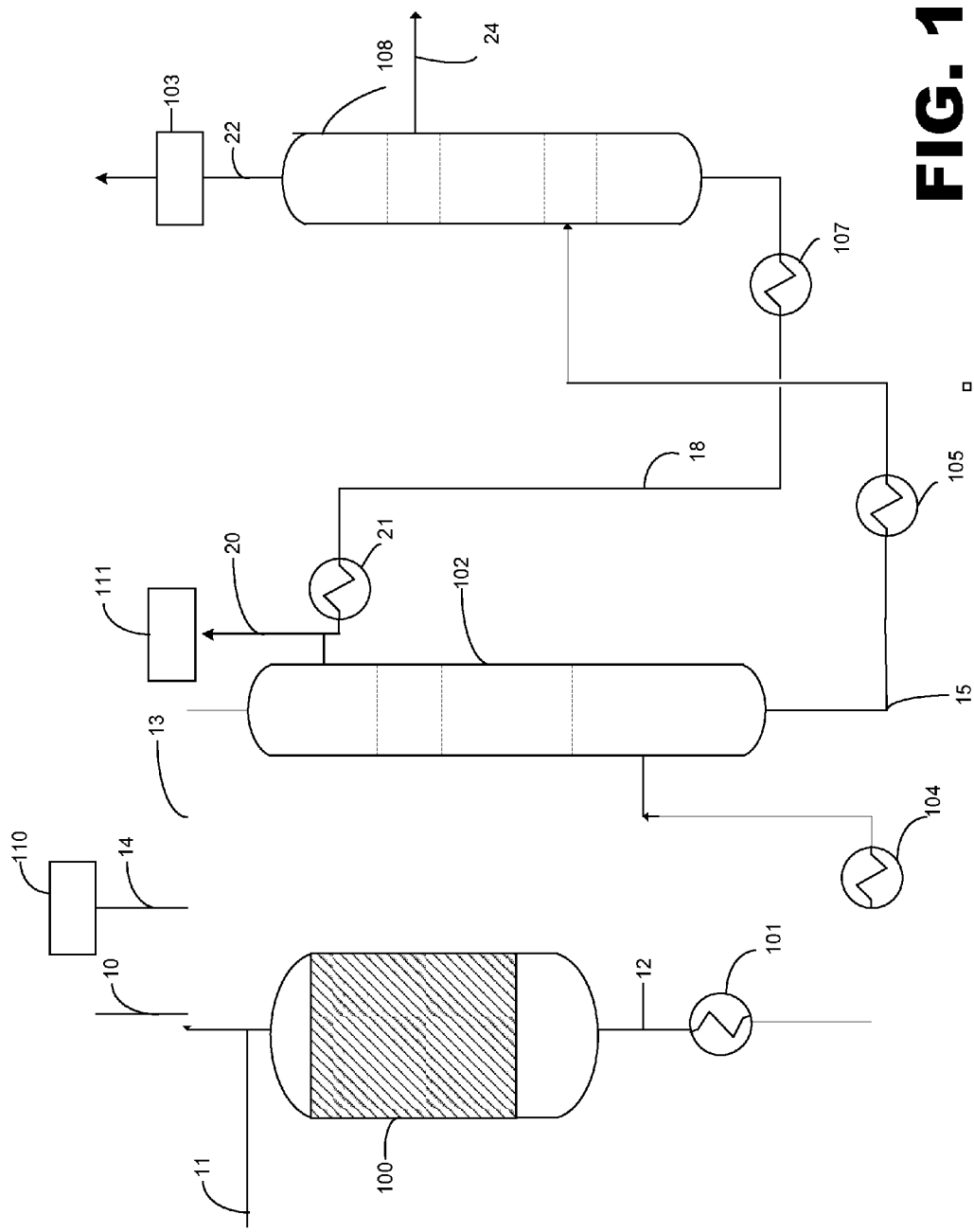
FIG. 1 depicts a process flow diagram for conversion of propylene to acrolein in accordance with an iteration of the invention.

The present invention provides a process for the production of acrolein via the catalytic oxidation of propylene. The process advantageously utilizes a recycle step in the production of acrolein and a recycle step in the recovery of acrolein. Each of these recycle steps provides significant improvements to the overall production and recovery of acrolein.

For production of acrolein, the process generally involves use of propylene, an oxygen source with a high concentration of oxygen (instead of air), and recycle of the non-condensable portion ("recycle gas stream") from the reaction effluent gas stream (after acrolein removal). The recycle gas stream contains oxygen, unreacted propylene, propane, water, carbon dioxide, and carbon monoxide. Via use of the recycle gas stream and a feed of substantially pure oxygen, there is little or no need to feed steam as a diluent, because the recycle gas stream provides significantly all of the required diluent including sufficient water to satisfy the recommended minimum water feed to the catalyst. Use of substantially pure oxygen instead of air combined with the recycle gas stream substantially reduces the gas purge. Moreover, because unreacted propylene is recycled, the operating conditions of the reactor/catalyst may be run at more optimal conditions, such as at a lower temperature. Running the reactor at the lower temperature, for example, results in improved reaction selectivity and improved catalyst life.

The invention also provides improvements in acrolein recovery via use of a second recycle step. In this regard, the second recycle step allows for the build up of acrylic acid in the aqueous stream ("liquid recycle stream"), which is used as a solvent to separate acrolein via facilitating its absorption from the reaction effluent gas stream. In some embodiments, the acrylic acid concentration, for example, may be greater than about 25% by weight of the liquid recycle stream. It has been found that higher concentrations of acrylic acid in this stream results in a stream that is a more effective absorbent for acrolein compared to streams having lower concentrations of acrylic acid.

I. Acrolein Production

The production of acrolein according an iteration of the invention generally involves feeding an initial gas stream comprising an oxygen source, a propylene source, and, optionally, an anhydrous diluent to a reactor comprising a catalyst capable of oxidizing propylene to produce a reaction effluent gas stream. The reaction effluent gas stream comprises acrolein and other components, including, but not limited to, oxygen, carbon monoxide, carbon dioxide, acrylic acid, acetic acid, water, acetaldehyde, and unreacted propylene. As detailed more fully below, the reaction effluent gas stream is fed to the bottom section of a first separation device where the condensable portion of the reaction effluent gas stream is condensed to provide an aqueous liquid stream and a recycle gas stream. The recycle gas stream comprises the non-condensable portion of the reaction effluent gas stream and generally comprises water, oxygen, propylene, propane, carbon dioxide, and carbon monoxide. The recycle gas stream is advantageously fed back into the reactor where it serves as a diluent and provides an opportunity to improve overall propylene conversion (via passing unreacted propylene back through the reactor). Moreover, the recycle gas stream eliminates the need to add steam as a reaction diluent. By not adding steam, the size of the aqueous waste stream is greatly decreased.

(a) Initial Gas Stream

The amount of oxygen present in the oxygen source used in the initial gas stream can and will vary. In this regard, the oxygen source may be oxygen-enriched air or substantially pure oxygen. In some embodiments, for example, the oxygen source may comprise trace amounts of argon. In an embodiment, the oxygen source may comprise at least about 30 mole percent oxygen. In another embodiment, the oxygen source may comprise at least about 40 mole percent oxygen. In still another embodiment, the oxygen source may comprise at least about 50 mole percent oxygen. In a further embodiment, the oxygen source may comprise at least about 60 mole percent oxygen. In yet another embodiment, the oxygen source may comprise at least about 70 mole percent oxygen. In an additional embodiment, the oxygen source may comprise at least about 80 mole percent oxygen. In a further embodiment, the oxygen source may comprise at least about 90 mole percent oxygen. In yet another embodiment, the oxygen source may comprise at least about 95 mole percent oxygen. It still another embodiment, the oxygen source may comprise at least about 97 mole percent oxygen. In an additional embodiment, the oxygen source may comprise at least about 99 mole percent oxygen.

The amount of propylene present in the propylene source used in the initial gas stream can and will vary. For example, the propylene source may comprise varying mixtures of propylene, propane, and other light hydrocarbons. In one embodiment, the propylene source may comprise at least about 60 mole percent propylene. In another embodiment, the propylene source may comprise at least about 65 mole percent propylene. In an additional embodiment, the propylene source may comprise at least about 70 mole percent propylene. In another embodiment, the propylene source may comprise at least about 75 mole percent propylene. In an additional embodiment, the propylene source may comprise at least about 80 mole percent propylene. In yet another embodiment, the propylene source may comprise at least about 85 mole percent propylene. In a further embodiment, the propylene source may comprise at least about 90 mole percent propylene. In another embodiment, the propylene source may comprise at least about 95 mole percent propylene. In a further embodiment, the propylene source may comprise at least about 97 mole percent propylene. In yet another embodiment, the propylene source may comprise at least about 99 mole percent propylene.

The initial gas stream may optionally comprise an anhydrous diluent. The necessity of including the anhydrous diluent can and will depend to some extent on the composition of the oxygen source and/or the propylene source. In this regard, for example, the oxygen source may comprise argon and the propylene source may comprise propane. Both argon and propane, if present in the required amounts, may function as a diluent in the initial gas stream, thus negating the need to add the anhydrous diluent. If necessary, however, several anhydrous diluents are suitable for use in the present invention. As used herein, the term "anhydrous diluent" generally means a diluent that comprises only trace amounts of water, such as for example, less than about 10%. Suitable diluents, in addition to being anhydrous, are also typically inert, which means the diluent does not substantially react with any other reactants present in the initial gas stream or the recycle stream. A non-exhaustive list of suitable anhydrous diluents includes methane, propane, ethane, carbon dioxide, nitrogen, and carbon monoxide. The recycle gas stream may also function as an anhydrous diluent.

Generally speaking, the molar ratio of the oxygen source to the propylene source present in the initial gas stream at the reactor inlet can and will vary depending on the catalyst and reaction parameters. The molar ratio of the oxygen source to the propylene source, however, will typically range from about 1:1 to about 3:1. In one embodiment, the molar ratio of the oxygen source to the propylene source is 1:1. In an additional embodiment, the molar ratio of the oxygen source to the propylene source is 1.5:1. In a further embodiment, the molar ratio of the oxygen source to the propylene source is 2:1. In yet another additional embodiment, the molar ratio of the oxygen source to the propylene source is 2.5:1. In another, the molar ratio of the oxygen source to the propylene source is 3:1. The amount of anhydrous diluent, if present, ranges from about 70% to about 95% by volume, such as about 70% to about 75%, about 75% to about 80%, about 80% to about 85%, about 85% to about 90%, or about 90% to about 95% by volume.

(b) Recycle Gas Stream

The recycle gas stream, as detailed above, comprises the non-condensable portion of the reaction effluent gas stream and generally comprises oxygen, propylene, propane, water (in the form of steam), carbon dioxide, and carbon monoxide. Typically, the water in the recycle gas stream is greater than at least about 2% but less than about 10%, such as, for example, about 3%, about 4%, about 5%, about 6%, about 7%, about 8%, or about 9%.

The recycle gas stream is generally taken as an overhead stream from the first separation device and is combined with propylene and oxygen (i.e., the initial gas stream) and fed into the reactor inlet with the balance being either recycle gas or an inert diluent or a mixture of both. In certain embodiments, after the process achieves steady-state operation, the recycle gas stream may be subjected to purge prior to being combined with the initial gas stream and fed into the reactor inlet. As used herein, "purge" and "blow down" are used interchangeably. In some embodiments, about 25% of the recycle gas stream is purged and about 75% of the recycle gas stream is combined with the initial gas stream and fed into the reactor inlet. In other embodiments, about 20% of the recycle gas stream is purged and about 80% of the recycle gas stream is combined with the initial gas stream and fed into the reactor inlet. In yet other embodiments, about 15% of the recycle gas stream is purged and about 85% of the recycle gas stream is combined with the initial gas stream and fed into the reactor inlet. In still other embodiments, about 10% of the recycle gas stream is purged and about 90% of the recycle gas stream is combined with the initial gas stream and fed into the reactor inlet. In additional embodiments, about 5% of the recycle gas stream is purged and about 95% of the recycle gas stream is combined with the initial gas stream and fed into the reactor inlet. In other embodiments, about 2.5% of the recycle gas stream is purged and about 97.5% of the recycle gas stream is combined with the initial gas stream and fed into the reactor inlet. In various embodiments, the percent of recycle gas stream purged is about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, or about 2.5%.

One of the many advantages of using the gas recycle stream is that it may provide substantially all of the diluent needed for the oxidation reaction, thus minimizing or eliminating all together the need for adding any additional anhydrous diluent in the initial gas stream once the process has achieved steady-state operation. As used herein, "steady-state operation" means composition and process parameters are not changing substantially over time. In certain embodiments, the gas recycle stream provides at least about 75% of the diluent necessary for the oxidation reaction. In other embodiments, the gas recycle stream provides at least about 80% of the diluent necessary for the oxidation reaction. In additional embodiments, the gas recycle stream provides at least about 85% of the diluent necessary for the oxidation reaction. In other embodiments, the gas recycle stream provides at least about 90% of the diluent necessary for the oxidation reaction. In yet other embodiments, the gas recycle stream provides at least about 95% of the diluent necessary for the oxidation reaction. In other embodiments, the gas recycle stream provides at least about 97% of the diluent necessary for the oxidation reaction. In further embodiments, the gas recycle stream provides at least about 99% of the diluent necessary for the oxidation reaction.

(c) Reactor and Catalyst

The initial gas stream and recycle gas stream (once generated) are generally fed into an inlet of a reactor that contains a catalyst capable of oxidizing propylene to acrolein. Generally speaking, the type of reactor is not critical. In this regard, the reactor may be a fixed-bed, tubular reactor with liquid coolant passed through the shell. In other embodiments, fluidized bed reactors may also be employed. In yet a further embodiment, a multi-tube reactor may be used. The multi-tubular reactor may comprise tube diameters of about 10 mm to about 40 mm, or more preferably, about 22 mm to about 26 mm, which permit efficient removal of the heat of reaction. In typical operation, a heat transfer fluid, such as a molten salt bath, may be used to transfer heat during acrolein production. Any transfer fluid used in this process should be stable at the temperatures of reaction.

The choice of the catalyst is not a limiting feature of the invention. In this regard, any catalyst capable of oxidizing propylene to acrolein may be selected. Typically, the catalyst selected is a metal oxide or mixed metal oxides that are acrolein-selective in that they catalyze the oxidation of propylene so as to give predominantly acrolein as the reaction product. In some embodiments, the catalysts in general contain, as the main components, molybdenum, bismuth, and iron in an oxide form. In other embodiments, the catalysts may contain molybdenum, bismuth, iron, nickel and/or cobalt and optionally may include Be, Mg, Zn, Ba Ca, Sr, Na, K, Rb, Cs, Sn, Cr, Ge, Al, Ga, In, rare earth metals, Nb, Ta, Mn, Re, Pt, Pd, Ru, Rh, Ir, Tl, Ag, U, P, Ti, Sb and/or As. Non-exhaustive examples of suitable catalysts are disclosed in U.S. Pat. Nos. 3,825,600, 3,649,930, 4,031,135, 4,339,355, 5,077,434, 5,198,578, 5,218,146, and 6,057,481, all of which are hereby incorporated by reference in their entirety. The catalyst is generally in the solid phase and supported on, or mixed with, inert carriers such as silica, silicates, aluminum oxides or hydrated aluminum oxides, titanium dioxide, or zirconium oxides. In addition, the catalyst may be in a variety of forms such as pellets, spheres, or rings.

The oxidation reaction conditions, namely temperature, pressure, and gas hourly space velocity, in the reactor can and will vary. In this regard, the oxidation of propylene in the reactor may occur at a temperature ranging from about 250° C. to about 450° C. In various embodiments, the temperature may be about 250° C., about 260° C., about 270° C., about 280° C., about 290° C., about 300° C., about 310° C., about 320° C., about 330° C., about 340° C., about 350° C., about 360° C., about 370° C., about 380° C., about 390° C., about 400° C., about 410° C., about 420° C., about 430° C., about 440° C., or about 450° C. A variety of methods may be employed to control the reaction temperature. One illustrative example for controlling the reaction temperature is through the use of one or more salt baths. In this example, the catalyst is generally packed into several tubes that are submerged in a molten salt bath, which is used to cool the tubes. The salt bath may be HITEC® salt, a eutectic mixture of potassium nitrate, sodium nitrite, and sodium nitrate.

The overall operating outlet pressure of the reactor also can and will vary. In certain embodiments, the outlet operating pressure may be subatmospheric. In other embodiments, the outlet operating pressure may be atmospheric. In yet another embodiment, the outlet operating pressure may be superatmospheric. In another embodiment, the inlet operating pressure may range from about 20 psia to about 100 psia. In various embodiments, the inlet operating pressure may be about 20 psia, about 25 psia, about 30 psia, about 35 psia, about 40 psia, about 45 psia, about 50 psia, about 55 psia, about 60 psia, about 65 psia, about 70 psia, about 75 psia, about 80 psia, about 85 psia, about 90 psia, about 95 psia, or about 100 psia.

The operating pressure at the reactor inlet and outlet may be different and can and will vary. Due to a pressure drop through the system, the inlet pressure is typically greater than the outlet pressure. For example, in one embodiment the pressure at the reactor inlet may be from about 30 psia to about 40 psia and the pressure at the reactor outlet may be about 15 psia to about 25 psia. In another embodiment, the pressure at the reactor inlet may be from about 20 psia to about 30 psia and the pressure at the reactor outlet may be about 5 psia to about 15 psia. In yet an additional embodiment, the pressure at the reactor inlet may be about 25 psia and the pressure at the reactor outlet may be about 10 psia.

Flow rates may be varied to achieve the desired contact times between the catalyst and substrates (e.g., oxygen and propylene). As used herein, "contact time" is defined as the ratio of the open volume in the catalyst bed to the process volumetric flow at process conditions. Contact times may vary from about 0.2 to about 2.0 seconds. In various embodiments, the contact time may be about 0.2 seconds, about 0.3 seconds, about 0.4 seconds, about 0.5 seconds, about 0.6 seconds, about 0.7 seconds, about 0.8 seconds, about 0.9 seconds, about 1.0 seconds, about 1.1 seconds, about 1.2 seconds, about 1.3 seconds, about 1.4 seconds, about 1.5 seconds, about 1.6 seconds, about 1.7 seconds, about 1.8 seconds, about 1.9 seconds, or about 2.0 seconds.

The gas hourly space velocity within the reactor also can and will vary. As used herein "gas hourly space velocity" refers to the flow rate of the gases divided by the volume of the catalyst and is calculated at standard conditions. In one embodiment, the gas hourly space velocity may range from about 800 $hr^{-1}$ to about 2000 $hr^{-1}$. In various embodiments, the gas hourly space velocity may be about 800 $hr^{-1}$, about 825 $hr^{-1}$, about 850 $hr^{-1}$, about 875 $hr^{-1}$, about 900 $hr^{-1}$, about 925 $hr^{-1}$, about 950 $hr^{-1}$, about 975 $hr^{-1}$, about 1000 $hr^{-1}$, about 1025 $hr^{-1}$, about 1050 $hr^{-1}$, about 1075 $hr^{-1}$, about 1100 $hr^{-1}$, about 1125 $hr^{-1}$, about 1150 $hr^{-1}$, about 1175 $hr^{-1}$, about 1200 $hr^{-1}$, about 1225 $hr^{-1}$, about 1250 $hr^{-1}$ about 1275 $hr^{-1}$ about 1300 $hr^{-1}$ about 1325 $hr^{-1}$ about 1350 $hr^{-1}$ about 1375 $hr^{-1}$ about 1400 $hr^{-1}$ about 1425 $hr^{-1}$ about 1450 $hr^{-1}$ about 1475 $hr^{-1}$ about 1500 $hr^{-1}$ about 1525 $hr^{-1}$ about 1550 $hr^{-1}$ about 1575 $hr^{-1}$ about 1600 $hr^{-1}$ about 1625 $hr^{-1}$ about 1650 $hr^{-1}$ about 1675 $hr^{-1}$ about 1700 $hr^{-1}$ about 1725 $hr^{-1}$ about 1750 $hr^{-1}$ about 1775 $hr^{-1}$ about 1800 $hr^{-1}$ about 1825 $hr^{-1}$ about 1875 $hr^{-1}$ about 1900 $hr^{-1}$ about 1925 $hr^{-1}$ about 1950 $hr^{-1}$ about 1975 $hr^{-1}$ or about 2000 $hr^{-1}$.

As stated above, the product of the oxidative reaction taking place in the reactor is a reaction effluent gas stream comprising predominantly acrolein, oxygen, propylene, and several reaction by-products. The reaction by-products include water, carbon monoxide, carbon dioxide, acetaldehyde, acetic acid, and acrylic acid. Generally speaking, the reaction effluent gas stream is typically cooled prior to acrolein recovery to prevent subsequent reactions of acrolein and loss of product. For example, the reaction effluent gas stream may pass from the bottom of the reactor to a cooler, which decreases the temperature to about 150° C. to about 250° C. Even when cooled to this temperature, the reaction effluent gas stream remains a gaseous mixture.

Propylene conversion taking place in the reactor can and will vary. In one embodiment, from about 50 to about 98 mole percent of propylene is converted to acrolein in a single pass. In another embodiment, from about 70 to about 90 mole percent of propylene is converted to acrolein in a single pass. In various embodiments, about 50, about 60, about 70, about 80, or about 90 mole percent of propylene is converted to acrolein in a single pass. In alternate embodiments, the overall conversion of propylene to acrolein is about 80 to about 90 mole percent. In still another embodiment, the overall conversion of propylene to acrolein is about 80 to about 97 mole percent. In various embodiments the overall conversion of propylene to acrolein is about 80, about 81, about 82, about 83, about 84, about 85, about 86, about 87, about 88, about 89, about 90, about 91, about 92, about 93, about 94, about 95, about 96, or about 97 percent.

The yield of the catalyst for acrolein over any other oxidation product may advantageously be improved in accordance with various embodiments of the invention compared to acrolein manufacturing processes that do not utilize the recycle gas stream. Stated another way, the yield of the catalyst over any other oxidation product in accordance with certain embodiments of the invention may be improved compared to acrolein manufacturing processes that are single pass. In this regard, the yield of the catalyst in certain embodiments of the invention may improve by about 0.5%, about 0.75%, about 1.0%, about 1.25%, about 1.50%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, or greater about 5.0% compared to single pass processes. In this context, the yield is an overall yield and is equal to the conversion times selectivity.

II. Acrolein Recovery Via First and Second Separation Devices

The recovery of acrolein according to an iteration of the invention generally involves the use of two separation devices. The reaction effluent gas stream (after being optionally cooled) is generally fed to the bottom section of the first separation device. In the first separation device, the reaction effluent gas stream is typically separated into a condensable portion and a non-condensable portion. The non-condensable portion becomes the recycle gas stream discussed in section I(b) and generally comprises oxygen, propylene, propane, water (humidity, which is water in the form of vapor), carbon dioxide, and carbon monoxide. The condensable portion becomes the aqueous liquid stream, which generally comprises acrolein, acrylic acid, acetic acid, water, and acetaldehyde. The aqueous liquid stream is fed to the second separation device where it is fractionated into a low-boiling point impurity stream, a liquid recycle stream, and an acrolein stream. "Fractionate" as used herein refers to separating a material into portions based on boiling point. A portion of the liquid recycle stream, which in some embodiments comprises from about 20% to about 30% by weight acrylic acid after the process achieves steady-state operation, is typically fed to the top of the first separation device where it aids in the absorption of acrolein from the reaction effluent gas stream. The acrolein may then be recovered from the second separation device by any means known in the art.

(a) First Separation Device

As stated above, the reaction effluent gas stream, after being optionally cooled, generally enters the bottom section of the first separation device. Suitable first separation devices may comprise a variety of sizes and shapes to the extent the device is capable of absorbing the reaction effluent gas stream into a condensable portion (which becomes part of the aqueous liquid stream) and a non-condensable portion (which becomes the recycle gas stream). In one embodiment, the first separation device comprises an absorber column or a quench/scrubber column. The quench/scrubber may rapidly cool (quench) the hot reaction effluent gases and absorb (scrub) condensable components in the cooled reaction effluent stream.

The temperature and pressure within the first separation device can and will vary. In this regard, the overhead temperature may range from about 20° C. to about 75° C. In various embodiments, the overhead temperature is about 20° C., about 25° C., about 30° C., about 35° C., about 40° C., about 45° C., about 50° C., about 55° C., about 60° C., about 65° C., about 70° C., or about 75° C. The base pressure within the first separation device may range from about 5 psia to about 45 psia. In various embodiments, the pressure is about 5 psia, about 10 psia, about 15 psia, about 20 psia, about 25 psia, about 30 psia, about 35 psia, about 40 psia, or about 45 psia.

After the reaction effluent gas stream enters the bottom section of the first separation device, it separates into a non-condensable portion, which becomes part of the recycle gas stream, and a condensable portion, which dissolves and becomes part of the aqueous liquid stream. The recycle gas stream typically exits the top portion of the first separation device, is subjected to an optional purge, and then is fed back to the reactor after being mixed with the initial gas stream (as more fully detailed in section I(b)). The aqueous liquid stream generally exits the bottom portion of the first separation device and is typically fed approximately to the middle section of the second separation device. Generally, the aqueous liquid stream comprises acrolein, acrylic acid, acetaldehyde, and water. In various embodiments, once the process achieves steady-state operation, the amount of each component as a weight percentage of the aqueous liquid stream is as follows: acrolein may range from about 1% to about 6%, acrylic acid may range from about 15% to about 45%, acetaldehyde may range from 0.01% to about 0.5%, and water may range from about 55% to about 85%. Optionally, to reduce the occurrence of fouling, the aqueous recycle stream may contain a water-soluble polymerization inhibitor, as described below in Section II(b).

In one embodiment, the aqueous liquid stream is flashed prior to entry into the second separation device. Flashing generally results in more than 50% of the non-condensables (dissolved gasses) being vaporized. In alternate embodiments, greater than 60%, greater than 70%, greater than 80%, or greater than 90% of the non-condensables are vaporized and removed from the process. The remaining flashed aqueous liquid stream is fed to the second separation device. Flashing the aqueous liquid stream may offer advantages in operating temperatures of the overhead condenser in the second separation device by allowing for operation of the overhead condenser at more moderate temperatures. The flasher may be operated at a range of 5 psia to 25 psia. In various embodiments, the flasher is operated at 5 psia, 10 psia, 15 psia, 20 psia, or 25 psia. The flasher may be operated at a temperature ranging from about 50° C. to about 90° C. In various embodiments the flasher may be operated at about 50° C., about 60° C., about 70° C., about 80° C. or about 90° C.

(b) Second Separation Device

The aqueous liquid stream, as stated above, is typically fed to middle section of the second separation device. Suitable second separation devices may comprise a variety of sizes and shapes to the extent the device is capable of fractionating the aqueous liquid stream into a low-boiling point impurity stream, an acrolein stream, and a liquid recycle stream. In one embodiment, the second separation device comprises a desorber/fractionater column. The desorber/fractionater column generally will comprise a reboiler, an overhead condenser, and one or more overhead receivers. In certain embodiments, the second separation device may comprise at least one side-draw take-off outlet located between the inlet for the feed of the aqueous liquid stream and the portion of the second separation device, comprising the low-boiling point impurity stream. The desorber/fractionater column may contain physical trays or packing to achieve the targeted separation.

The temperature and pressure in the second separation device can and will vary. In this regard, the second separation device is generally run under subatmospheric pressure with an overhead pressure ranging from about 5 to about 14 psia. The second separation device, however, may also be run at about atmospheric pressure. The temperature within the second separation device can and will vary. In this regard, the base temperature of the device may be from about 50° C. to over about 100° C., and the temperature of the condenser and the overhead receiver may be held between about 10° C. to about −50° C.

In certain embodiments, a polymerization inhibitor is added to the overhead condenser and/or the overhead receiver of the second separation device. Suitable polymerization inhibitors are generally known and non-limiting examples include manganese acetate, dialkylthiocarbamic acid copper salts, hydroquinone, 4-hydroxy-2,2,6,6-tetramethylpiperidin-1-oxyl(4-hydroxy-TEMPO, or 1-$\lambda$1-oxidanyl-2,2,6,6-tetramethylpiperidin-4-ol), and derivatives thereof. In some embodiments, the polymerization inhibitor is added as a dilute solution comprising the polymerization inhibitor, acetic acid, and water. The dilute solution may comprise from about 1%-3% polymerization inhibitor, from about 3% to about 8% acetic acid, and from about 95%-99% water. In one embodiment, the dilute solution comprises 2% polymerization inhibitor, 5% acetic acid, and 93% water. In another embodiment, the polymerization inhibitor is added as a dilute acrolein solution. In another embodiment, the inhibitor is added as an aqueous only solution. In such embodiments, the polymerization inhibitor in the second separation device may be added at a rate that achieves an inhibited liquid (in the column) that contains inhibitor at 50 ppm, 75 ppm, 100 ppm, 125 ppm, 150 ppm, 175 ppm, 200 ppm or higher concentration. The aqueous liquid stream may also contain a polymerization inhibitor. The polymerization inhibitor used in the overhead receiver and in the aqueous liquid stream fed to the second separation device may be the same or different from each other.

An additional inhibitor can optionally be added below the acrolein stream. The inhibitor added to the overhead receiver and below the acrolein stream may be the same or different. In one embodiment, hydroquinone is added to the overhead receiver of the second separation device and a solution comprising 4-hydroxy TEMPO is added below the acrolein stream. In some embodiments, an aqueous solution of 4-hydroxy TEMPO is added 1, 2, 3, 4, 5, or 6 trays below the acrolein stream.

After the aqueous liquid stream is fed to second separation device operating under conditions detailed herein, the stream is separated via fractionation into the low-boiling point impurity stream, the acrolein stream, and the liquid recycle stream. The second separation device may be run under total reflux, and the only overhead product is the low-boiling point impurity stream, which is a vapor stream leaving the overhead receiver. In some embodiments, about 100% of the material is condensed by the overhead condenser and is pumped back to the top tray of the second separation device. The low-boiling point stream comprises at least 60% of the total acetaldehyde from the aqueous liquid stream with the remainder ending up in the acrolein stream. The low-boiling point stream may optionally be purged to an incinerator. Generally, the liquid recycle stream, which comprises water and substantially all of the acrylic acid from the aqueous liquid stream, separates to the bottom portion of the second separation device. The acrolein stream, which contains substantially all of the acrolein from the aqueous liquid stream, separates to approximately the bottom of the upper third portion of the second separation device, which is below the low-boiling point impurity stream and above the liquid recycle stream, for example, below the top tray and above the feed point tray.

The acrolein stream in certain embodiments may be recovered from the second separation device as a vapor side stream through at least one side-draw take-off outlet. In other embodiments, the acrolein stream in certain embodiments may be recovered from the second separation device as a liquid side stream through at least one side-draw take-off outlet. In various embodiments, the acrolein stream comprises less than about 0.6% by weight acetaldehyde, less than about 0.55% by weight acetaldehyde, less than about 0.5% by weight acetaldehyde, less than about 0.45% by weight acetaldehyde, less than about 0.4% by weight acetaldehyde, less than about 0.35% by weight acetaldehyde, less than about 0.3% by weight acetaldehyde, less than about 0.25% by weight acetaldehyde, less than about 0.2% by weight acetaldehyde, less than about 0.15% by weight acetaldehyde, less than about 0.1% by weight acetaldehyde, or less than about 0.05% by weight acetaldehyde.

Figure 2:
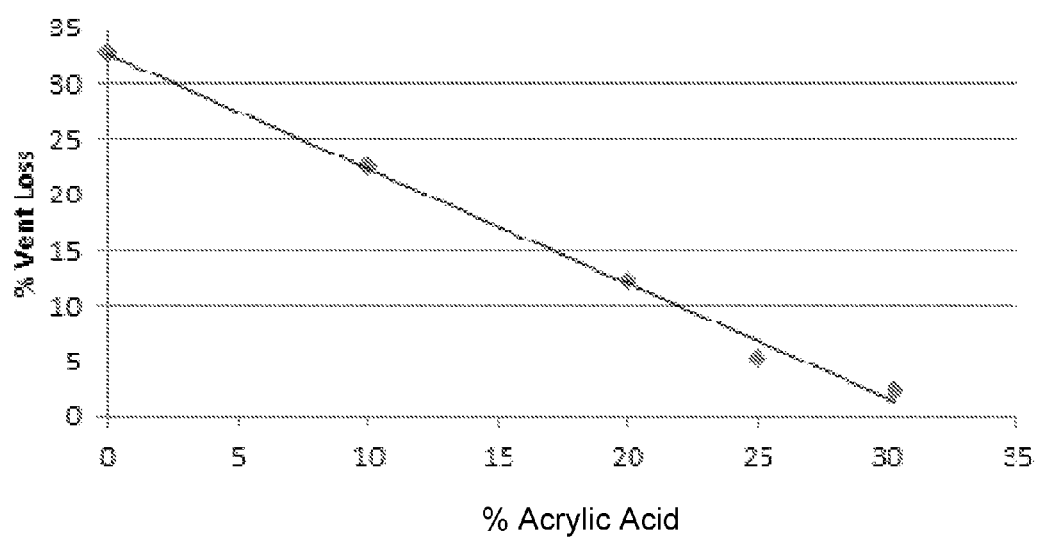
FIG. 2 shows the relationship between acrylic acid in the liquid recycle stream and propionaldehyde loss. The propionaldehyde loss shows an inverse linear relationship to the percentage by weight of acrylic acid in the aqueous recycle. Propionaldehyde is a surrogate for acrolein.

The liquid recycle stream typically comprises substantially all of the water and acrylic acid present from the aqueous liquid stream. After the process reaches steady-state operation, the liquid recycle stream may comprise about 10% by weight acrylic acid, about 15% by weight acrylic acid, about 20% by weight acrylic acid, about 25% by weight acrylic acid, about 30% by weight acrylic acid, about 35% by weight acrylic acid, about 40% by weight acrylic acid, about 45% by weight acrylic acid, or greater than 50% by weight acrylic acid. In other embodiments, the liquid recycle stream may comprise from about 10% to about 50% by weight acrylic acid. In another embodiment, the liquid recycle stream may comprise from about 15% to about 40% by weight acrylic acid. In yet another embodiment, the liquid recycle stream may comprise from about 10% to about 40% by weight acrylic acid. In certain embodiments, the liquid recycle stream comprises from about 10% to about 15% by weight acrylic acid, from about 15% to about 20% by weight acrylic acid, from about 20% to about 25% by weight acrylic acid, from about 25% to about 30%, from about 30% to about 35% by weight acrylic acid. In yet another embodiment, the liquid recycle stream may comprise from about 20% to about 30% by weight acrylic acid or from about 25% to about 35% by weight acrylic acid. In one embodiment, acrolein yields correspond linearly with the amount of acrylic acid in the liquid recycle stream. FIG. 2 illustrates a linear relationship with propionaldehyde (i.e., an acrolein surrogate) loss where acrylic acid content in the liquid recycle stream is varied from about 0% to about 30% by weight.

The liquid recycle stream is generally taken from the bottom of the second separation device and fed into the top portion of the first separation device. The weight ratio of liquid recycle to the reaction effluent gas stream entering the first separation device is from about 2:1 to about 10:1, or more preferably about 3:1 to about 5:1. In certain embodiments, a portion of the liquid recycle stream is optionally purged prior to being fed to the first separation device. In some embodiments, about 25% of the liquid recycle stream is purged and about 75% of the liquid recycle stream is fed into the first separation device. In other embodiments, about 20% of the liquid recycle stream is purged and about 80% of the liquid recycle stream is fed into the first separation device. In yet other embodiments, about 15% of the recycle stream is purged and about 85% of the liquid recycle stream is fed into the first separation device. In still other embodiments, about 10% of the recycle stream is purged and about 90% of the liquid recycle stream is fed into the first separation device. In additional embodiments, about 5% of the recycle stream is purged and about 95% of the liquid recycle stream is fed into the first separation device. In other embodiments, about 2.5% of the recycle stream is purged and about 97.5% of the liquid recycle stream is fed into the first separation device. In still another embodiment, about 1.5% of the recycle stream is purged and about 98.5% of the recycle stream is fed into the first separation device. In yet another embodiment, about 1% of the recycle stream is purged and about 99% of the recycle stream is fed into the first separation device.

One of the many advantages of the liquid recycle stream is that it allows for the build-up of high concentrations of acrylic acid. It has been found that higher concentration of acrylic acid in this stream, when fed back to the first separation device, provides a stream that is a more effective absorbent for acrolein compared to streams having lower concentrations of acrylic acid.

III. Illustrative Embodiment of Acrolein Production and Recovery

FIG. 1 discussed below provides an example of an iteration of the invention for producing and recovering acrolein. This example is one of several iterations of the present invention and should not be construed as limiting the invention's scope.

With reference to FIG. 1, an initial gas stream 11 is combined with a recycle gas stream 13 at a pressure of about 30 psia. The initial gas stream 11 comprises a propylene source and an oxygen source. An optional anhydrous diluent may be added as shown by stream 10. The propylene source comprises at least about 95 vol. % propylene. The oxygen source comprises at least about 99 vol. % oxygen. The combined gas stream (i.e., stream 11 and stream 13) comprises 5 to 30 vol. propylene, 9 to 30 vol. % oxygen, 0.1 to 15 vol. % percent propane, 10 to 40 vol. carbon dioxide, 15 to 45 vol. % carbon monoxide, and 2 to 10 volume percent water vapor and is fed to acrolein reactor 100 where about 90 mole percent of the propylene is converted to acrolein, various byproducts, and water over a mixed molybdenum-bismuth-iron-oxide catalyst at about 280° C. Acrobin reactor 100 is a liquid-cooled, multitube reactor, wherein the catalyst is in the tubes. The liquid used to cool the multitube reactor is a molten salt bath. The reaction effluent gas steam 12 comprises acrolein and other components including, but not limited to, oxygen, carbon monoxide, carbon dioxide, acrylic acid, acetic acid, water, acetaldehyde, and unreacted propylene. The reaction effluent gases exiting the reactor may be cooled to about 160° C., for example, by exchanging heat against condensate (water) in a steam generator 101. Reaction effluent gas stream 12 may also pass through a secondary heat exchanger 104 to further reduce the temperature of the stream.

The cooled reaction effluent gas stream 12 may be fed to the bottom portion of a first separation device 102, comprising a quench/scrubber column. Within the first separation device 102, the reaction effluent gas stream 12 is contacted directly with the liquid recycle stream 18 resulting in the reaction effluent gas stream being divided into a condensable portion, which is dissolved in and becomes a part of the aqueous liquid stream 15, and a non-condensable portion, which becomes the recycle gas stream 13. The liquid recycle stream 18 comprises water and at least about 20% by weight acrylic acid and, optionally, a polymerization inhibitor, such as a few hundred parts-per-million 4-hydroxy TEMPO. The aqueous liquid stream 15 may be withdrawn from the base of the first separation device 102 by a pump and pumped through heat exchanger 105 where it gives up some of its heat to cooling water. Before entering the first separation device 102, liquid recycle stream 18 may pass through a heat exchanger 107 where it gives up some of its heat to cooling water. The overhead temperature in the first separation device 102 may be about 50° C. The bottom pressure in the first separation device 102 may be 25 psia. The weight ratio of liquid recycle stream 18 to the effluent gas stream 12 entering the first separation device 102 is about 4:1.

Recycle gas stream 13 comprises unreacted oxygen and propylene, propane, carbon monoxide, carbon dioxide, and water vapor with small amounts of organic compounds exits the top portion of the first separation device 102. Recycle gas stream 13 is compressed in recycle compressor wherein it is pressurized from about 15 psia to about 60 psia. A portion of the recycle gas stream 13 is purged as off-gas stream 14. Off-gas stream 14 may be incinerated in a combustor 110, and the incineration products may be vented to the atmosphere. The remaining portion of recycle gas stream 13 is combined with the initial gas stream 11 and fed to the reactor inlet. In this way, recycle gas steam 13 provides at least about 85 vol. % of the total feed for the propylene oxidation reaction. Off-gas stream 14 is about 0% to about 5% of the total volume of gases leaving the top of the first separation device 102.

The aqueous liquid stream from the first separation device, stream 15, comprises about 55% to 85% by weight water, 15% to 35% by weight acrylic acid, about 1 to 6% by weight acrolein, and about 0.01% to about 0.5% by weight acetaldehyde at a steady-state operation. Aqueous liquid stream 15 is withdrawn from the bottom of the first separation device 102 and may be pumped by a pump through heat exchanger 105 where heat is transferred from stream 15. Aqueous liquid stream 15 is fed to a second separation device 108, which comprises a desorber/fractionater column.

The second separation device 108 operates at a temperature of from about 100° C. at the bottom and about 20° C. at the ϕp. The second separation device 108 may operate at a pressure from about 5 psia to about 15 psia. The condenser and overhead receiver of the second separation device may be held at a temperature between 10° C. and −50° C.

In the second separation device 108, the aqueous liquid stream 15 is separated into an acrolein stream 24, a low-boiling point stream 22, and a liquid recycle stream 18. Liquid recycle stream 18 comprises about 70% by weight water and about 30% by weight acrylic acid. Liquid recycle stream 18 is withdrawn from the base of the second separation device 108 by a pump. Liquid recycle stream 18 may be further split into stream 20, which flows to the acrylic acid recovery or disposal system 111. Optionally, heat exchanger 21 may be used.

Low-boiling point impurity stream 22 exits the second separation device 108 overhead as a vapor. The noncondensable gases and volatile organics leaving the second separation device 108 are routed to combustor 103 for incineration. Stream 24 is the acrolein stream and may be recovered from the second separation device as a liquid or vapor side-draw through one or more side-draw take-off outlets. Acrolein stream 24 is specification grade acrolein and may be further purified if desired.

EXAMPLES

Example 1

Modeled Continuous Process

A continuous process for producing acrolein was modeled using software from Aspen Technologies. The simulation was run with a propylene source (95-97 mole % propylene), an oxygen source (90-95 mole % oxygen), diluent, and recycle gas. This reaction produced a liquid aqueous stream 15 after passage through the first separation device 102, and an acrolein product stream after passage through the second separation device 108. Exemplary compositions and characteristics of each of these streams are shown below in Table I.

TABLE I

|  | Unit | Propylene Source | Oxygen Source | Diluent | Recycle Gas | Liquid recycle | Acrolein Product |
| --- | --- | --- | --- | --- | --- | --- | --- |
| Total Mass Rate | lb/hr | 2859 | 2480 | 106 | 25262 | 124169 | 3044 |
| Propylene | mole % | 93.0 | 0 | 0 | 0.3 | 0 | 0 |
| Oxygen | mole % | 0 | 95.0 | 0 | 3.9 | 0 | 0 |
| Nitrogen | mole % | 0 | 0.5 | 0 | 2.1 | 0 | 0 |
| Water | mole % | 0 | 0 | 0 | 7.9 | 89.3 | 6.4 |
| Acrolein | mole % | 0 | 0 | 0 | 0.02 | 0 | 93.45 |
| Carbon monoxide | mole % | 0 | 0 | 0 | 12.8 | 0 | 0 |
| Acrylic Acid | mole % | 0 | 0 | 0 | 0.4 | 9.8 | 0 |
| Carbon dioxide | mole % | 0 | 0 | 0 | 15.4 | 0 | 0 |
| Acetaldehyde | mole % | 0 | 0 | 0 | 0.03 | 0 | 0.13 |
| Allyl alcohol | mole % | 0 | 0 | 0 | 0.05 | 0.2 | 0.02 |
| Propane | mole % | 7.0 | 0 | 0 | 15.2 | 0 | 0 |
| Acetic acid | mole % | 0 | 0 | 0 | 0.1 | 0.7 | 0 |
| Argon | mole % | 0 | 4.5 | 0 | 18.5 | 0 | 0 |
| Methane | mole % | 0 | 0 | 100.0 | 23.3 | 0 | 0 |
| Temperature | ° F. | 77.0 | 77.0 | 77.0 | 233.3 | 150.8 | 96.1 |
| Pressure psia | psia | 180.0 | 64.7 | 50.0 | 35.0 | 34.0 | 35.0 |
| Vapor Frac |  | 0 | 1.0 | 1.0 | 1.0 | 0 | 0 |
| Liquid Frac |  | 1.0 | 0 | 0 | 0 | 1.0 | 1.0 |
| Solid Frac |  | 0 | 0 | 0 | 0 | 0 | 0 |
| Density lb/cuft | lb/ft$^3$ | 31.7 | 0.4 | 0.1 | 0.2 | 59.8 | 51.6 |
| Average MW | lb/lb-mole | 42.2 | 32.3 | 16.0 | 32.0 | 23.7 | 53.6 |

Still in reference to FIG. 1, a liquid recycle stream from the second separation device 108 is fed to the first separation device 102 to maintain near 100% recovery of the acrolein from the effluent of acrolein reactor 100. To maintain material balance around the process, three purge streams are used: an off-gas stream 14, a low-boiling point impurity stream 22, and a water purge 20. Exemplary rates and compositions of these purge streams are given in Table II.

TABLE II

| | Unit | Off-Gas Stream | Low-boiling Point Impurities | Water Purge |
|---|---|---|---|---|
| Total Mass Rate | lb/hr | 605 | 192 | 1617 |
| Propylene | mole % | 0.3 | 0.5 | 0 |
| Oxygen | mole % | 3.9 | 0.8 | 0 |
| Nitrogen | mole % | 2.1 | 0.03 | 0 |
| Water | mole % | 7.9 | 0 | 89.3 |
| Acrolein | mole % | 0.02 | 2.3 | 0 |
| Carbon monoxide | mole % | 12.8 | 2.2 | 0 |
| Acrylic acid | mole % | 0.4 | 0 | 9.8 |
| Carbon dioxide | mole % | 15.4 | 11.3 | 0 |
| Acetaldehyde | mole % | 0.03 | 10.7 | 0 |
| Allyl alcohol | mole % | 0.05 | 0 | 0.2 |
| Propane | mole % | 15.2 | 33.6 | 0 |
| Acetic acid | mole % | 0.07 | 0 | 0.7 |
| Argon | mole % | 18.5 | 0.6 | 0 |
| Methane | mole % | 23.33 | 37.97 | 0 |
| Temperature F. | ° F. | 233.3 | −22.0 | 184.5 |
| Pressure psia | psia | 35.0 | 6.2 | 35.0 |
| Vapor Frac | | 1.00 | 1.00 | 0 |
| Liquid Frac | | 0.00 | 0.00 | 1.0 |
| Solid Frac | | 0.00 | 0.00 | 0 |
| Density lb/cuft | lb/ft$^3$ | 0.15 | 0.04 | 58.5 |
| Average MW | lb/lb-mole | 32.0 | 33.2 | 23.7 |

Example 2

Lab Quench/Scrubber (First Separation Device) Example

A 40 tray 1" glass vacuum jacketed and silvered Oldershaw column was equipped with a 160° C. vapor feed which entered a quench chamber at the base of the column and a liquid recycle feed to the top tray of the column. The quench chamber was a 12" section of 316SS Propak dump packing in a 1" vacuum jacketed and silvered packed column section. Liquid from the column base reservoir was pumped through a refrigerated condenser and then through an electrical preheater before entering the top of the packing (i.e., quench chamber). This permitted the adjustment of the recirculation/quench fluid to any desired temperature. Reactor gas feed to the column was simulated by mixing a liquid stream comprising reactants in the amounts listed in Table III with nitrogen and heating to 160° C. in a tube furnace (i.e., a flasher). The mixture fed to the flasher is referred to as organic feed and is understood to mimic compositions produced in the acrolein reactor. This synthetic hot reaction gas (organic feed) was fed to the bottom of the packed section (i.e., quench chamber). The column residue was removed from the base reservoir through a refrigerated condenser via an IVEK pump and collected in a weighed receiver. The liquid feed to the vaporizer was fed via an IVEK pump from a weighed feed container. The nitrogen feed rate to the vaporizer was controlled by a mass flow controller. The gas exiting the top of the column passed thru a two stage dry ice trap to collect the condensable material for quantification and analysis. The liquid recycle stream was fed to the top tray of the column via an IVEK pump from a weighed container. An electrical preheater was used to adjust the temperature of the aqueous liquid stream prior to injection to the top tray. By weighing the liquid feed to the flasher (input into the column), liquid recycle stream and residue stream (condensables) along with the material caught in the dry ice trap, a complete liquid mass balance could be performed on the column.

To minimize heat losses from the system, both the packing section and tray section of the column were loosely traced with electrical heat tape and then insulated with 1" fiberglass insulation. Thermocouples were placed on the wall and under the heating tape to monitor temperatures. The wall temperatures were adjusted to the expected internal temperatures of the two different column sections (tray section 38° C. and packed section 56° C.). The Oldershaw feed section on the top of the column was also traced and insulated. A heat lamp was shined on the base reservoir to prevent excessive heat loss from the non-insulated reservoir and glass adaptor at the base of the quench section.

Heat losses around the flasher were also controlled by placing heat tapes on all of the lines. Also both the nitrogen and liquid feed to the flasher were preheated. The flasher itself was a 1" diameter 316 SS tubing packed with 316 SS Propak dump packing. The packed tubing was ~18" long and was heated via a tube furnace. The liquid and nitrogen feeds were introduced to the top of the packing using a tube inside a tube arrangement. This flasher system allowed a synthetic reactor gas mix to be fed to the quench section of the column at the desired 160° C.

The liquid recycle stream was 30.3% acrylic acid, 1.8% acetic acid, 67.9% water and 500 ppm 4-hydroxy TEMPO. The liquid recycle stream feed rate was 6.2 g/min and the residue rate was 6.3 g/min. The liquid recirculation rate to the quench chamber was set at 7 g/min. The liquid feed rate to the flasher was 0.2 g/min along with a nitrogen feed rate of 0.96 L/min. The liquid feed to the flasher contained 76.2% acrolein, 16.5% acrylic acid, 4.4% water, 1.5% acetaldehyde, 1.4% acetic acid and 1000 ppm 4-hydroxy TEMPO. The column was brought up and operated for three hours and then a three hour mass balance was performed. The mass balance data is shown in Table Ill.

TABLE III

| | |
|---|---|
| Organic feed rate to flasher (g/min) | 0.2 |
| liquid recycle stream feed rate (g/min) | 6.2 |
| nitrogen feed rate to flasher (L/min) | 0.96 |
| residue take-off rate (g/min) | 6.3 |
| residue recycle rate (g/min) | 7 |
| liquid recycle temp (° C.) | 35 |
| recycle tray vapor temp (° C.) | 47 |
| flasher feed to column temp (° C.) | 160 |
| top tray vapor temp (° C.) | 35 |
| top of column outlet pressure (psig) | 0 |
| mass balance liquid recycle stream fed (g) | 1117 |
| mass balance flasher org feed fed (g) | 36.1 |
| mass balance residue removed (g) | 1134 |
| mass balance cold trap collected (g) | 6.1 |
| mass balance run time (hr) | 3 |
| % water in liquid recycle stream | 67.9 |
| % acrylic acid in liquid recycle stream | 30.3 |
| % acetic acid in liquid recycle stream | 1.8 |
| % water in organic feed to flasher | 4.4 |
| % acrolein in organic feed to flasher | 76.2 |
| % acrylic acid in organic feed to flasher | 16.5 |
| % acetaldehyde in organic feed to flasher | 1.5 |
| % acetic acid in organic feed to flasher | 1.4 |
| % water in residue take-off | 62.4 |
| % acrolein in residue take-off | 3.7 |
| % acetaldehyde in residue take-off | 0.034 |
| % acetic acid in residue take-off | 1.3 |
| % water in cold trap | 73.2 |
| % acrolein in cold trap | 16.2 |
| % acetaldehyde in cold trap | 0.51 |
| % acetic acid in cold trap | ND |
| % acrylic acid in cold trap | 10.1 |

Example 3

Lab Finishing Column (Second Separation Device) Example

A 60 tray 1" glass vacuum jacketed and silvered Oldershaw column was assembled with the feed 24 trays above the reboiler and the liquid side stream 21 trays above the feed tray. The lab reboiler was an electrically heated three leg thermosiphon reboiler. The overhead of the column was a total take-off line which was electrically traced to prevent condensation which could lead to fouling. The vapor from the overhead line was fed into a 5° C. Friedrich condenser for rapid cooling. The cooled liquid dripped into the jacketed receiver which was held at −20° C. All of the collected distillate was pumped to the top tray as cooled reflux for the column (i.e. the column was run on total reflux). The overhead receiver was equipped with a vacuum adaptor section which removed inert gases and any uncondensed vapor through a vent condenser (−20° C.) which returned some of the condensable material in the vent back to the overhead receiver. The vacuum for the column was supplied by a water aspiration pump. The pump was protected by a Dry Ice trap which removed any remaining condensable material. The column residue was removed from the reboiler through a condenser via an IVEK pump and collected in a weighed receiver. The column liquid side stream was removed via an IVEK pump and also collected in a weighed receiver. The feed to the column was electrically preheated and pumped into the column from a weighed feed container.

The inhibitor solution used in the column was a 2% 4-hydroxy TEMPO and 5% acetic acid in water solution which was added to the Friedrich condenser via a syringe pump. A small feed of nitrogen was injected into the bottom of the column to simulate the dissolved inert gases expected in the quench/scrubber residue (i.e. finishing column feed). The nitrogen flow rate was controlled by a mass flow meter. By weighing the feed, inhibitor solution, residue stream and side stream along with the material caught in the Dry Ice trap, a complete liquid mass balance could be performed on the column.

The column feed was inhibited with 100 ppm 4-hydroxy TEMPO. The column feed rate was 12.9 g/min with a 12.6 g/min residue rate and 0.3 g/min liquid side stream rate. Column boil-up was adjusted to give a reflux rate of 2.3 mL/min. The column overhead pressure was 700 torr. The column was brought up and run for three hours then a three hour mass balance was performed. The mass balance data for the three finishing column runs are shown in Table IV.

TABLE IV

| Rate Number | A | B | C |
|---|---|---|---|
| Feed rate (g/min) | 12.9 | 12.9 | 12.9 |
| Residue rate (g/min) | 12.6 | 12.6 | 12.6 |
| Liquid side stream rate (g/min) | 0.3 | 0.3 | 0.3 |
| Reflux rate (mL/min) | 2.3 | 2.3 | 2.3 |
| Inhibitor feed rate (g/hr) | 0.6 | 0.6 | 0.6 |
| Overhead pressure (torr) | 700 | 700 | 700 |
| Reboiler liquid temp (° C.) | 106 | 101.3 | 101.6 |
| Feed preheater liquid temp (° C.) | 41 | 37 | 38 |
| Feed tray vapor temp (° C.) | 92 | 94 | 61 |
| Side stream vapor temp (° C.) | 50 | 50 | 50 |
| Overhead vapor temp (° C.) | 39 | 47 | 47 |
| Overhead receiver jacket fluid temp (° C.) | −18 | −20 | −20 |
| Overhead Condenser jacket fluid temp (° C.) | 5 | 3 | 3 |
| $N_2$ feed rate to reboiler (L/hr) | 0.6 | 1 | 1 |
| Mass balance feed (g) | 2329 | 2324 | 2330 |
| Mass balance residue (g) | 2266 | 2271 | 2269 |
| Mass balance side stream (g) | 53.4 | 53.2 | 53 |
| Mass balance overhead vapor in cold trap (g) | 1.3 | 0.5 | 0.6 |
| Mass balance run time (hrs) | 3 | 3 | 3 |
| % Water in feed | 65.7 | 65.4 | 68.3 |
| % Acrylic acid in feed | 29.8 | 30.6 | 27.6 |

TABLE IV-continued

| Rate Number | A | B | C |
|---|---|---|---|
| % Acrolein in feed | 2.6 | 2.5 | 2.6 |
| % Acetic acid in feed | 1.8 | 1.5 | 1.4 |
| % Acetaldehyde in feed | 0.035 | 0.03 | 0.019 |
| % Water in residue | 67.4 | 66.9 | 68 |
| % Acrylic acid in residue (bottoms) | 30.6 | 31.2 | 30.3 |
| % Acetic acid in residue (bottoms) | 1.9 | 1.8 | 1.7 |
| % Acrolein in residue (bottoms) | 0.096 | 0.07 | 0.09 |
| % Acetaldehyde in residue (bottoms) | 0.007 | 0.0007 | 0.001 |
| % Water in liquid side stream | 2.5 | 2.5 | 2.3 |
| % Acrylic acid in liquid side stream | ND | ND | ND |
| % Acrolein in liquid side stream | 97.2 | 97.4 | 97.6 |
| % Acetic acid in liquid side stream | ND | ND | 0.01 |
| % Acetaldehyde in liquid side stream | 0.33 | 0.15 | 0.086 |
| % Water in reflux | 1.5 | 2 | 2 |
| % Acrylic acid in reflux | ND | ND | ND |
| % Acrolein in reflux | 52.3 | 80.9 | 80.1 |
| % Acetic acid in reflux | ND | 0.04 | 0.05 |
| % Acetaldehyde in reflux | 46.2 | 16.7 | 17.4 |
| % Water in overhead vapor | 0.21 | 0.4 | 0.4 |
| % Acrylic acid in overhead vapor | ND | ND | ND |
| % Acrolein in overhead vapor | 14 | 41.6 | 44 |
| % Acetic acid in overhead vapor | ND | 0.06 | 0.06 |
| % Acetaldehyde in overhead vapor | 85.8 | 58 | 55.5 |

Example 4

Impact of Liquid Recycle Stream Acrylic Acid Concentration on Acrolein Recovery in Quench/Scrubber The apparatus described in Example 2 was run under the same flow rate conditions as Example 2 using the acrolein surrogate, propionaldehyde. The propionaldehyde was present in the liquid feed to the flasher at the same concentration as acrolein in Example 3. The acrylic acid concentration in the liquid recycle stream was varied from 30.3% to 0% (i.e. pure water) in runs D-H. Table V contains the temperature profile and propionaldehyde losses observed for these runs. FIG. 4 is a plot of vent loss (i.e. propionaldehyde loss in the column overhead stream) versus acrylic acid concentration in the scrubbing solution for these runs and shows a linear relationship between higher percentages of acrylic acid in the aqueous liquid stream and low propionaldehyde loss.

TABLE V

| Run | D | E | F | G | H |
|---|---|---|---|---|---|
| % Acrylic acid in liquid recycle stream | 30.3 | 25 | 20 | 10 | 0 |
| % Propionaldehyde loss | 2.5 | 5.4 | 12.3 | 22.6 | 32.8 |
| Liquid recycle T (° C.) | 35 | 35 | 35 | 34 | 35 |
| Recycle tray vapor T (° C.) | 41 | 41 | 41 | 41 | 41 |
| Top tray vapor T (° C.) | 36 | 36 | 36 | 35 | 35 |
| Liquid Recycle Stream T (° C.) | 36 | 36 | 36 | 35 | 35 |
| Tray wall T (° C.) | 38 | 39 | 38 | 38 | 38 |
| Quench section wall T (° C.) | 45 | 45 | 45 | 45 | 45 |
| Top feed section wall T (° C.) | 38 | 38 | 38 | 38 | 38 |

What is claimed is:

1. A continuous process for producing acrolein, the process comprising:
   (a) feeding an initial gas stream comprising an oxygen source, and a propylene source to a reactor comprising a catalyst under conditions such that propylene is oxidized to produce a reaction effluent gas stream, the reaction effluent gas stream comprising acrolein, oxygen, propylene, carbon monoxide, carbon dioxide, acrylic acid, acetic acid, water, and acetaldehyde;

(b) feeding the reaction effluent gas stream to the bottom section of a first separation device, the condensable portion of the reaction effluent gas stream being condensed in the first separation device to provide an aqueous liquid stream and a recycle gas stream, the condensable portion of the reaction effluent gas stream becoming the aqueous liquid stream comprising acrolein, acrylic acid, acetic acid, water and acetaldehyde, the non-condensable portion of the reaction effluent gas stream becoming the recycle gas stream comprising oxygen, propylene, propane, carbon dioxide, and carbon monoxide;

(c) feeding a portion of the recycle gas stream to the reactor of step (a);

(d) feeding the aqueous liquid stream to a second separation device that fractionates the aqueous liquid stream into a low-boiling point impurity stream, an acrolein stream, and a liquid recycle stream, the low-boiling point impurity stream comprising acetaldehyde, the acrolein stream comprising substantially pure acrolein, and the liquid recycle stream comprising water, acetic acid, and acrylic acid; and (e) feeding a portion of the liquid recycle stream to the top of the first separation device of step (b), the liquid recycle stream comprising from about 20% to about 30% acrylic acid by weight.

2. The process of claim 1, wherein the oxygen source of the initial gas stream comprises at least 95 mole percent oxygen.

3. The process of claim 1, wherein the catalyst is an oxide catalyst containing molybdenum, bismuth, and iron.

4. The process of claim 1, wherein the propylene conversion in the reactor of step (a) is from about 50% to about 98%.

5. The process of claim 1, wherein the reaction yield of step (a) for acrolein is improved at least 2% compared to a process having all of the steps detailed in claim 1 except for the recycle gas of step (c).

6. The process of claim 1, wherein the aqueous liquid stream of step (b) comprises from about 1% to about 6% acrolein, from about 15% to about 45% acrylic acid, from about 0.01% to about 0.5% acetaldehyde, and from about 55% to about 85% water.

7. The process of claim 1, wherein the amount of acetaldehyde in the acrolein stream of step (d) is less than about 0.3% by weight.

8. The process of claim 1, wherein the amount of acrylic acid in the liquid recycle stream of step (e) is about 30% by weight.

9. The process of claim 1, wherein the recycle liquid stream of step (e) is fed into the first separation device at a weight ratio of 2:1 to 10:1 relative to the reaction effluent gas stream of step (a).

10. The process of claim 1, wherein at least one polymerization inhibitor is added to the overhead receiver of the second separation device.

11. The process of claim 10, wherein the polymerization inhibitor is hydroquinone.

12. The process of claim 1, wherein the reaction effluent gas stream of step (a) is cooled to a temperature of from about 200° C. to about 280° C. prior to feeding the stream into the first separation device of step (b).

13. The process of claim 1, wherein the first separation device of step (b) is operated at a temperature ranging from about 20° C. to about 75° C., and at a pressure of from about 15 psia to about 45 psia.

14. The process of claim 1, wherein the second separation device of step (d) is operated at a base temperature ranging from about 50° C. to about 100° C., and at a pressure of from about 5 psia to about 14 psia.

15. The process of claim 1, wherein the yield of acrolein is at least 80%.

16. The process of claim 1, wherein the yield of acrolein is at least 85%.

* * * * *